United States Patent [19]
Sletzinger et al.

[11] 3,981,911
[45] Sept. 21, 1976

[54] PROCESS FOR PREPARING (1-OXO-2-CYCLOPENTYL-2-METHYL-6,7-DICHLORO-5-INDANYLOXY)ACETIC ACID

[75] Inventors: Meyer Sletzinger, North Plainfield; George G. Hazen, Westfield, both of N.J.

[73] Assignee: Merck & Co., Inc., Rahway, N.J.

[22] Filed: Feb. 15, 1974

[21] Appl. No.: 442,696

[52] U.S. Cl. .................. 260/520 C; 260/332.1; 260/332.2 A; 260/332.3 P; 260/326.5 B; 260/347.3; 260/347.4; 260/468 G; 260/473 F; 260/514 G; 260/590 FA
[51] Int. Cl.² .................. C07C 65/14; C07C 69/95
[58] Field of Search ............ 260/520, 473 F, 520 D, 260/590 FA, 520 C

[56] References Cited
UNITED STATES PATENTS 3,668,241   6/1972   Cragoe et al. .................. 260/473 F
3,704,314   11/1972  Cragoe et al. .................. 260/520

OTHER PUBLICATIONS

Beilstein, Band 7 (1925) pp. 360–363.
Elsevier's, "Encyclopedia of Organic Chemistry," (1948) vol. 12 A pp. 103–106, 219.

Primary Examiner—Norman Morgenstern
Attorney, Agent, or Firm—Michael C. Sudol, Jr.; James A. Arno; J. Jerome Behan

[57] ABSTRACT

A process for preparing (1-oxo-2-cyclopentyl-2-methyl-6,7-dichloro-5-indanyloxy)acetic acid comprising reacting 5-cyclopentyl-5-methyl-2-cyclopentenone with a 4-carbon conjugated (open or cyclic) diene bearing vicinal chlorines adjacent to an ether group; aromatizing the resulting adduct to yield the desired indanone.

6 Claims, No Drawings

PROCESS FOR PREPARING (1-OXO-2-CYCLOPENTYL-2-METHYL-6,7-DICHLORO-5-INDANYLOXY)ACETIC ACID

BACKGROUND OF THE INVENTION

This invention relates to a process for preparing (1-oxo-2-cyclopentyl-2-methyl-6,7-dichloro-5-indanyloxy)acetic acid, (I, below) and the nontoxic pharmaceutically acceptable salt, ester and amide derivatives thereof.

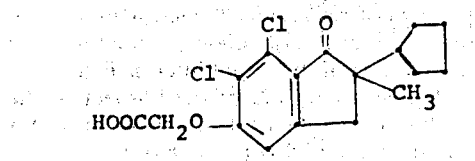

I nuclear substituted aralkyl having from 7 to about 20 carbon atoms; and wherein X is SO, SO$_2$, O, NH, or X represents two hydrogen atoms.

The indanone of structure I and the nontoxic pharmaceutical acceptable salt, ester and amide derivatives thereof are diuretics, saluretics and uricosuric agents.

Thus, it is an object of the present invention to provide a specific, highly efficient unified process for the preparation of (1-oxo-2-cyclopentyl-2-methyl-6,7-dichloro-5-indanyloxy)acetic acid and its nontoxic pharmaceutically acceptable salt, ester and amide derivatives. It is also an object of the present invention to provide useful intermediates (II, above) which are involved in the process of this invention.

DETAILED DESCRIPTION OF THE INVENTION

The process aspect of the present invention may most conveniently be described by the following schematic overview:

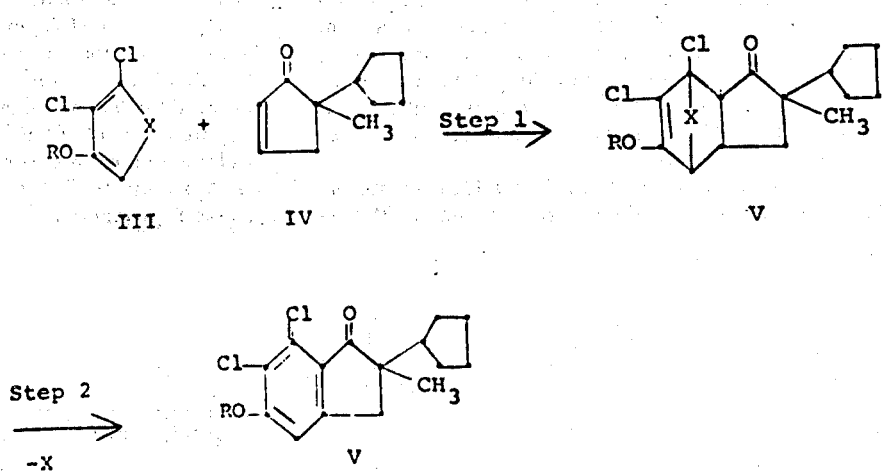

This invention also relates to useful intermediates involved in the preparation of I having the structure:

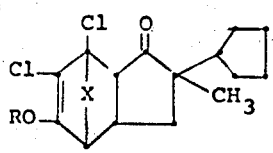

II wherein R is CH$_2$COOH, R' or CH$_2$COOR' and wherein R' is lower alkyl having from 1 to about 6 carbon atoms, phenyl or substituted phenyl, aralkyl or nuclear substituted aralkyl, having from 7 to about 20 carbon atoms; and wherein X is two hydrogen atoms SO$_2$, SO, O, NH. There is no criticality as to the precise identity of R' other than that it be compatible with the desired course of reaction since the function of R' is merely that of a blocking or protective group. However, for purposes of this invention the most preferred R' radicals for R and H (when R is CH$_2$COOR'); lower alkyl, such as methyl, ethyl, isopropyl and propyl; aryl such as phenyl, and nitrophenyl; and aralkyl such as benzyl, and p-chlorobenzyl.

In words relative to the above diagram, the dienophile (5-cyclopentyl-5-methyl-2-cyclopentenone, IV) is reacted with a 4-carbon conjugated diene or cyclic diene bearing vicinal chlorines adjacent to an ether group (step 1); elimination of hydrogens and other substituents (X) from the resulting adduct gives the desired indanone, V. With respect to the indanone product, if R is R' or CH₂COOR' the desired (1-oxo-2-cyclopentyl-2-methyl-6,7-dichloro-5-indanyloxy)acetic acid is obtainable by hydrolysis and treatment with halo acetic acid or by simple hydrolysis, and acidification, respectively.

In further description of Step 1, the most preferred X substituents are H₂, SO₂, SO and O. The reaction solvent and the temperature of reaction are not considered critical aspects of the instant unified scheme of synthesis inasmuch as any solvent which is inert or substantially inert to the reactants and products may be employed. In this regard it is been found that solvents such as methylene chloride, hexane, benzene, chlorobenzene and decalin are particularly preferred. The temperature of reaction may range from about 20° to about 300°C. and is preferably from about 20° to about 100°C. Preferably the reaction is conducted in sealed vessel at pressures of from about 1 to about 10 atmospheres. Typically the reaction is complete in from 1 to about 24 hours. Further, in Step 1, the molar ratio of reactants, III:IV may range from about 5:1 to about 1:5 and preferably is about 1:1.

With respect to Step 2, aromatization by elimination of X from the adduct resulting from Step 1 is accomplished by well known methods. Suitable aromatizing agent which may be employed in Step 2 include: sulfur, selenium, palladium catalysts, platinum catalysts, quinone, and the like. The elimination may also be effected by simple heating.

In further description of Step 2, suitable solvents may be selected from a wide group of which methylene chloride, hexane, benzene, chlorobenzene and decalin are particularly preferred. Typically the reaction is conducted at a temperature in the range of from about 25° to about 300°C. In the case wherein X is SO or SO₂, aromatizing agents may be selected from any strong base such as alkali and alkaline earth metal oxides, hydrous oxides, and lower alkoxides, for example, potassium-t-butoxide, sodium ethoxide, sodium methoxide, potassium hydroxide and the like; suitable solvents in this aspect include any inert, polar solvent such as dimethylsulfoxide, lower alkanol, tetrahydrofuran, dioxane, dimethylformamide, and the like.

The following examples specifically illustrate but do not limit either the product or process aspects of the present invention. Further it is to be emphasized that while the examples specifically illustrate the process invention in terms of discrete steps such stepwise division is artificial and arbitrarily adopted as a means of furthering description of the useful intermediate product aspects. For in reality the process aspect of the present invention is a unified scheme of synthesis for (1-oxo-2-cyclopentyl-2-methyl-6,7-dichloro-5-indanyloxy)acetic acid and its nontoxic pharmaceutically acceptable salt, ester and amide derivatives.

Dienophile Preparation

The dienophile, 5-cyclopentyl-5-methyl-2-cyclopentenone (IV), in general is prepared by methylation of 2-cyclopentyl cyclopentenone or alkylation of 2-methyl-2-cyclopentenone with cyclopentylbromide followed by dehydrogenation. However, preferably it is prepared by acid or base catalyzed self condensation of cyclopentenone as described by Jormir Plesek, Chemical Abstracts 50 7732b (1956), and shown in the following flow diagram:

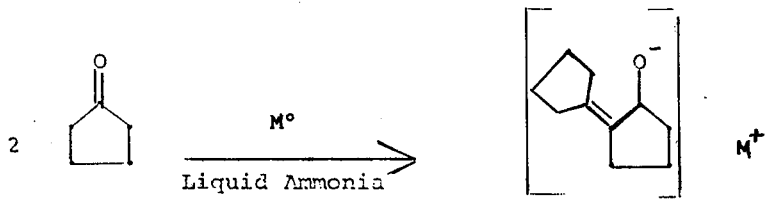

M° = alkali or alkaline earth metal

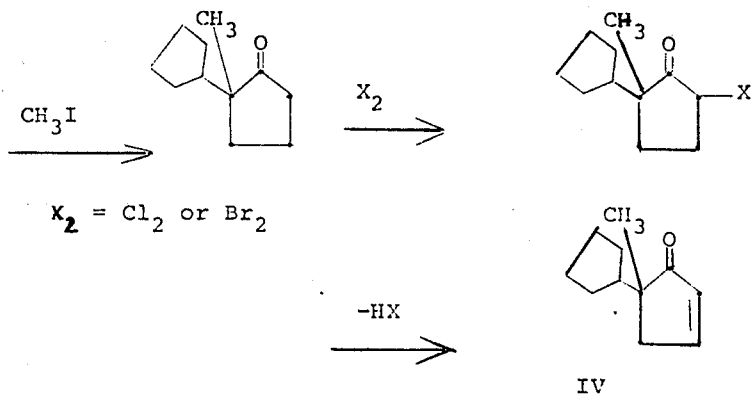

From the above diagram, the 2-cyclopentylidene cyclopentanone anion prepared by treating cyclopentanone with an alkali or alkaline earth metal in liquid ammonia is alkylated by methyl iodide in the manner of Stork

[Journal of the American Chemical Society, 87, pp 275–286 (1965)]. The 2-cyclopentyl-2-methyl-2-cyclopentenone is then dehydrogenated or halogenated and dehydrohalogenated to give the desired 5-cyclopentyl-5-methyl-2-cyclopentenone, IV.

EXAMPLE 1

Preparation of 2-cyclopentyl-2-methyl-cyclopentanone

A 500 ml. 3-neck flask fitted with a stirrer, Hirshberg dropping funnel, and dry ice condenser is heated for 15 minutes with a free flame. Dry nitrogen gas is swept through the system while heating for several additional minutes. The system is then evacuated and filled with nitrogen. Thereafter 150 ml. of ammonium is distilled into the reaction flask; 4 g. (0.048 moles) of cyclopentenone is introduced and stirring begun. Two equivalents (2.2 g.) of sodium metal is then added and resulting blue solution is stirred for one hour. Methyliodide (16 g., 0.11 mole) is then added drop wise turning the medium white. After an interval of 30 minutes, the dry ice condenser is replaced by a water condenser and the ammonia is allowed to evaporate overnight. The remaining salts are dissolved in 100 ml. of water, and the solution is made acidic by the addition of concentrated hydrochloric acid. The organic material is taken up in ether; the ether solution is washed with water, dried with anhydrous magnesium sulfate and concentrated under reduced pressure to give 4 g. of 2-cyclopentyl-2-methyl-cyclopentanone.

EXAMPLE 2

Preparation of 5-cyclopentyl-5-methyl-2-cyclopenteneone

Four grams (0.026 mole) of 2-cyclopentyl-2-methyl-cyclopentanone dissolved in 20 ml. of chloroform is cooled to 0°C. and 4.2 g. (0.026 mole) of bromine is added over a 40 minute interval. An aqueous 5 wt. % solution of sodium bisulfite is added to destroy the excess bromine followed by 10 wt. % aqueous sodium hydroxide solution to achieve a pH of 7. The aqueous layer is discarded after back extraction with 20 ml. of chloroform. After washing the combined chloroform layers with water and drying over magnesium sulfate, the chloroform is removed at reduced pressure. Pyridine, 20 ml., is added and the solution is refluxed for one hour, cooled and diluted with 100 ml. water. 100 Ml. of chloroform is added and the layers are separated. The chloroform layer is washed with 50 ml. of 6 molar HCl and then dried over magnesium sulfate. Evaporation gives 5-cyclopentyl-5-methyl-2-cyclopentenone suitable for use in the Diels-Alder reaction of Step 1.

EXAMPLE 3

Preparation of (1-oxo-2-cyclopentyl-2-methyl-6,7-dichloro-5-indanyloxy)acetic acid Chlorine (1 mole) is added to 1 mole of 1-methylene-2-propynyl methyl ether (enol ether of methyl propynyl ketone) in 1 l. of methylene chloride at 0°C. To the resulting 1,2-dichloro-3-methoxy-1,3-butadiene is added one mole of 5-cyclopentyl-5-methyl-2-cyclopentenone as prepared according to Example 1. After heating in a pressure vessel at 120°C. for 24 hours the solvent is evaporated under reduced pressure leaving II (above) wherein R is $CH_3$ and X represents 2 hydrogen atoms.

A mixture of 50 g. of the above compound 35 g. of 5% palladium on carbon and 1 l. of dry decalin is placed in a 3 l. round bottom flask and heated under reflux for 24 hours. The hot mixture is filtered by suction using a previously heated Buchner funnel and the filtrate is evaporated under reduced pressure to remove the decalin. The dark oil remaining is dissolved in 250 ml. of ethanol and 5 g. of activated charcoal is added; after 15 minutes stirring the solid components are removed by filtration and on cooling the filtrate yields the 5-methoxy derivative of the desired indanone, which melts at 110°–112°C.

25.0 Grams of the 2-cyclopentyl-2-methyl-5-methoxy-6,7-dichloro-1-indanone is heated for 7 hours at 85°C. in 100 g. of pyridine hydrochloride to provide the 5-hydroxy derivative. Thereafter 200 ml. of dimethylformamide, 100 g. of sodium carbonate and 0.105 moles of chloroacetic acid is added. The resulting (1-oxo-2-cyclopentyl-2-methyl-6,7-dichloro-5-indanyloxy) acetic acid is extracted with methylene chloride, isolated by evaporation of the methylene chloride, and recrystallized from glacial acetic acid.

EXAMPLE 4

Preparation of (1-oxo-2-cyclopentyl-2-methyl-6,7-dichloro-5-indanyloxy)acetic acid As in Example 3 except that the 1,2-dichloro-3-methoxy-1,3-butadiene is replaced by the corresponding carboxymethyleneoxy derivative and with the exception that the hydrolysis/acylation steps are omitted, the desired (1-oxo-2-cyclopentyl-2-methyl-6,7-dichloro-5-indanyloxy) acetic acid is obtained.

EXAMPLE 5

As in Example 3 except that the 1,2-dichloro-3-methoxy-1,3-butadiene is replaced by a diene having the structure:

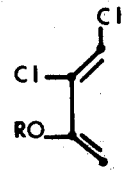

wherein R,

benzyl, and isopropyl, respectively, there is obtained after hydrolysis,

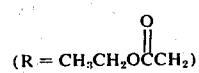

or hydrolysis and acylation (R = benzyl and isopropyl) an equivalent amount of (1-oxo-2-cyclopentyl-2-methyl-6,7-dichloro-5-indanyloxy)acetic acid, respectively.

EXAMPLE 6

Following the procedure exactly as described in Example 3 except that 4 g. of sulfur is substituted for the 5% palladium on carbon there is obtained an equivalent amount of (1-oxo-2-cyclopentyl-2-methyl-6,7-dichloro-5-indanyloxy)acetic acid.

EXAMPLE 7

Preparation of (1-oxo-2-cyclopentyl-2-methyl-6,7-dichloro-5-indanyloxy)acetic acid 1 Mole of a diene having the structure:

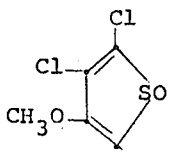

and 1 mole of 5-cyclopentyl-5-methyl-2-cyclopenten-1-one and 1 l. of benzene are refluxed for 6 hours. One liter of decalin is added along with 35 g. of 5% palladium on charcoal. The benzene is removed by distillation and the mixture is refluxed for 24 hours. The mixture is filtered by suction and the filtrate evaporated at reduced pressure to remove the decalin. To the resulting product is added 5 g. of activated charcoal and 50 ml. of ethanol at 60°C. On removal of the solid charcoal and cooling, the 5-methoxy derivative of the desired indanone separates with a melting point of 110°–112°C.

25.0 Grams of the 2-cyclopentyl-2-methyl-5-methoxy-6,7-dichloro-1-indanone is heated for 7 hours at 85°C. in 100 g. of pyridine hydrochloride to provide the 5-hydroxy derivative. Thereafter 200 ml. of dimethylformamide, 100 g. of sodium carbonate and 0.105 moles of chloroacetic acid is added. The resulting (1-oxo-2-cyclopentyl-2-methyl-6,7-dichloro-5-indanyloxy) acetic acid is extracted with methylene chloride, isolated by evaporation of the methylene chloride, and recrystallized from glacial acetic acid.

EXAMPLE 8

Following the procedure exactly as described in Example 7 except there is substituted for the conjugated diene of Example 7 a diene of the structure:

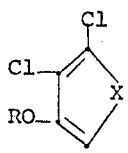

wherein R, is

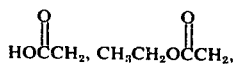

and benzyl, respectively, and wherein X is SO, SO₂, O and NH, respectively, there is obtained, respectively, the corresponding amount of (1-oxo-2-cyclopentyl-2-methyl-6,7-dichloro-5-indanyloxy)acetic acid directly (R is CH₂COOH) or following hydrolysis and isolation

or hydrolysis, acylation and isolation (R is benzyl).
What is claimed is:
1. A process for preparing (1-oxo-2-cyclopentyl-2-methyl-6,7-dichloro-5-indanyloxy)acetic acid of the structure:

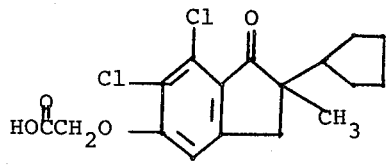

comprising the steps of
a. reacting under Diels-Alder conditions a conjugated diene of the structure:

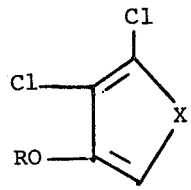

and 5-cyclopentyl-5-methyl-2-cyclopentenone in a substantially inert solvent, at a temperature of from 20° to 300°C. and at a pressure of 1 to 10 atmospheres; and
b. aromatizing the adduct obtained from Step (a) with the elimination of X; wherein R is CH₂COOH, R', or CH₂COOR' and wherein R' is lower alkyl; phenyl or substituted phenyl, aralkyl or nuclear substituted aralkyl having from 7 to about 20 carbon atoms; and wherein X represents two hydrogen atoms, SO, SO₂, O, or NH in an inert solvent at a temperature of 25° to 300°C.; and
c. if R is R' then hydrolyzing the resulting product from step (b) and treating with halo acetic acid to form the desired product and if R is CH₂COOR' hydrolyzing and acidifying the product of step (b) to obtain the desired product.
2. The process of claim 1 wherein R' is lower alkyl having from 1 to about 6 carbon atoms, phenyl, substituted phenyl; benzyl and nuclear substituted benzyl, and wherein X represents two hydrogen atoms, SO, SO₂, or O.
3. The process of claim 2 wherein the aromatizing of Step (b) is effected by treating the adduct of Step (a) with an aromatizing agent selected from the group consisting of sulfur, selenium, platinum and palladium.
4. The process of claim 2 wherein X is SO₂ or SO and the aromatizing of Step (b) is effected by treating the adduct of Step a. with a strong base.
5. The process of claim 4 wherein the strong base is selected from alkali and alkaline earth metal oxides, hydrous oxides and lower alkoxides.
6. A process for preparing (1-oxo-2-cyclopentyl-2-methyl-6,7-dichloro-5-indanyloxy)acetic acid of the structure:

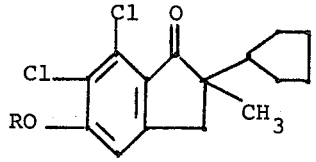

comprising the steps of
a. reacting under Diels-Alder conditions a conjugated diene of the structure:

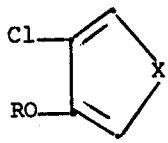

and 5-cyclopentyl-5-methyl-2-cyclopentenone in a substantially inert solvent, at a temperature of from 20° to 300°C. and at a pressure of 1 to 10 atmospheres; and b. aromatizing the adduct obtained from step (a) with the elimination of X; wherein R is $CH_2COOH$, R', or $CH_2COOR'$ and wherein R' is lower alkyl; phenyl or substituted phenyl, aralkyl or nuclear substituted aralkyl having from 7 to about 20 carbon atoms; and wherein X represents two hydrogen atoms, SO, $SO_2$, O, or NH in an inert solvent at a temperature of 25° to 300°C.

* * * * *